US005584296A

United States Patent [19]
Cui et al.

[11] Patent Number: 5,584,296
[45] Date of Patent: Dec. 17, 1996

[54] PATIENT SENSOR FOR OPTICAL CEREBRAL OXIMETERS AND THE LIKE

[75] Inventors: Weijia Cui, Troy; Richard S. Scheuing, Ann Arbor, both of Mich.

[73] Assignee: Somanetics Corporation, Troy, Mich.

[21] Appl. No.: 356,863

[22] Filed: Dec. 15, 1994

Related U.S. Application Data

[63] Continuation of Ser. No. 983,820, Dec. 1, 1992, abandoned.

[51] Int. Cl.⁶ .................................................. A61B 05/00
[52] U.S. Cl. .............................. 128/633; 128/666; 356/41
[58] Field of Search ...................... 128/633-4, 664-6; 356/41

[56] References Cited

U.S. PATENT DOCUMENTS

| | | | |
|---|---|---|---|
| 2,790,438 | 4/1957 | Taplin et al. | 128/633 |
| 3,230,951 | 1/1966 | Teschner | 128/666 |
| 3,602,213 | 8/1971 | Howell et al. | 128/633 |
| 3,769,974 | 11/1973 | Smart et al. . | |
| 3,810,460 | 5/1974 | Van Nie | 128/666 |
| 3,814,081 | 6/1974 | Mori | 128/2 L |
| 3,822,695 | 7/1974 | Takayama | 128/2 L |
| 3,910,701 | 10/1975 | Henderson et al. | 128/625 |
| 4,013,067 | 3/1977 | Kresse et al. . | |
| 4,015,595 | 4/1977 | Benjamin, Jr. | 128/2.05 V |
| 4,063,551 | 12/1977 | Sweeney . | |
| 4,091,803 | 5/1978 | Pinder | 128/2.05 P |
| 4,109,643 | 8/1978 | Bond et al. | 128/2 L |
| 4,163,447 | 8/1979 | Orr | 128/666 |
| 4,223,680 | 9/1980 | Jobsis | 128/633 |
| 4,249,540 | 2/1981 | Koyama et al. | 128/666 |
| 4,259,963 | 4/1981 | Huch | 128/635 |
| 4,267,844 | 5/1981 | Yamanishi | 128/633 |
| 4,281,645 | 8/1981 | Jobsis | 128/633 |
| 4,321,930 | 3/1982 | Jobsis et al. | 128/633 |
| 4,332,258 | 6/1982 | Arai et al. | 128/666 |
| 4,336,809 | 6/1982 | Clark | 128/665 |
| 4,344,438 | 8/1982 | Schultz | 128/634 |
| 4,350,163 | 9/1982 | Ford, Jr. et al. | 128/633 |
| 4,380,240 | 4/1983 | Jobsis et al. | 128/633 |
| 4,510,938 | 4/1985 | Jobsis et al. | 128/633 |
| 4,515,165 | 5/1985 | Carroll | 128/664 |
| 4,570,638 | 2/1986 | Stoddart et al. | 128/665 |
| 4,685,464 | 8/1987 | Goldberger et al. | 128/633 |
| 4,770,179 | 9/1988 | New, Jr. et al. | 128/633 |
| 4,805,623 | 2/1989 | Jobsis | 128/633 |
| 4,825,872 | 5/1989 | Tan et al. | 128/633 |
| 4,825,879 | 5/1989 | Tan et al. | 128/633 |
| 4,830,014 | 5/1989 | Goodman et al. | 128/665 |
| 4,840,179 | 6/1989 | Ulrich | 128/633 |
| 4,865,038 | 9/1989 | Rich et al. | 128/633 |
| 4,867,557 | 9/1989 | Takatami et al. | 356/41 |
| 4,880,304 | 11/1989 | Jaeb et al. | 356/41 |

(List continued on next page.)

FOREIGN PATENT DOCUMENTS

| | | | |
|---|---|---|---|
| 2517129 | 6/1976 | Germany | 356/32 |
| 2076963 | 12/1981 | United Kingdom | 128/2 L |
| WO8909566 | 10/1989 | WIPO | A61B 6/00 |

*Primary Examiner*—Angela D. Sykes
*Assistant Examiner*—Robert L. Nasser, Jr.
*Attorney, Agent, or Firm*—Price, Heneveld, Cooper, DeWitt & Litton

[57] ABSTRACT

An optical sensor for use in clinical patient examination by spectrophotometric apparatus, having a body with softly deformable material which is conformable to a selected area on the body of the patient and internally-mounted electro-optical source and receivers for obtaining patient pathology data by transmission of selected wavelengths through a tissue volume adjacent the selected area, including substantially non-deforming light-transfer members disposed in alignment with the source and detectors and between them and the patient, to provide substantially constant and unchanging light-transfer passages or conduits therebetween. In the most preferred form, the light-transfer members comprise generally tubular elements having light-reflective interior walls, and the sensor body comprises either a layered structure of opaque, soft polymeric foam or the like (e.g., cellular urethane) or a substantially one-piece, molded or other such structure of generally comparable or analogous material and characteristics.

35 Claims, 3 Drawing Sheets

U.S. PATENT DOCUMENTS

| | | | |
|---|---|---|---|
| 4,928,691 | 5/1990 | Nicolson et al. | 128/633 |
| 4,938,218 | 7/1990 | Goodman et al. | 128/633 |
| 4,964,408 | 10/1990 | Hink et al. | 128/633 |
| 5,080,098 | 1/1992 | Willelt et al. | 128/666 |
| 5,094,240 | 3/1992 | Muz | 128/633 |
| 5,111,817 | 5/1992 | Clark et al. | 128/633 |
| 5,139,025 | 8/1992 | Lewis et al. | 128/665 |
| 5,140,989 | 8/1992 | Lewis et al. | 128/665 |

PATIENT SENSOR FOR OPTICAL CEREBRAL OXIMETERS AND THE LIKE

CONTINUING DATA

This is a continuation of application Ser. No. 07/983,820 filed on Dec. 10, 1992, now abandoned.

CROSS REFERENCE TO RELATED CASES

This patent application is related to copending application Ser. No. 711,452, filed Jun. 6, 1991, now U.S. Pat. No. 5,217,113, which in turn is related to and a continuation-in-part of prior applications Ser. Nos. 329,945, 827,526 and 542,022 (now U.S. Pat. Nos. 5,139,025, 5,140,989 and 4,570,638 respectively), and this application is also related to copending application Ser. No. 711,147, filed Jun. 6, 1991, now abandoned. The disclosure of each such application is incorporated herein by reference.

TECHNICAL FIELD

This invention relates generally to optical spectrophotometric methods and apparatus, particularly as adapted for use in clinical in vivo procedures involving human patients; more particularly, the invention relates to a patient monitoring device which utilizes such methods, and still more particularly to a sensor for such device, comprising an optical component carrier which is applied to the patient and used as the patient-spectrophotometer interface, by which optical-response spectrophotometric data is obtained which embodies physiological information.

BACKGROUND

In the above-referenced related prior patents, optical spectrophotometric procedures and apparatus are disclosed and described for in vivo clinical application to human patients, as well as a potential broader range of subjects, by which important biomedical information may be obtained which is directly indicative of intrinsic, internal biological and physiological processes, conditions, tissue or substance composition or state, etc., and these prior patents generally contemplate use of certain "optical probes", i.e., optical component groupings and their mounting and carrying apparatus, by which the selected light wavelengths are emitted and applied to the patient and the resulting light is detected and monitored at various locations on the patient.

While one principal focus of these prior patents involves the use of such spectrophotometric techniques on human anatomy in a manner by which the relative spacing of the light-emitting and certain of the light-detecting elements was variable, the underlying significance of such spacing was the important consideration in this regard, and thus the disclosures in these patents also contemplate comparable or analogous sender-receiver configurations of fixed geometry. These configurations and underlying considerations are particularly addressed in prior application Ser. No. 329,945, now U.S. Pat. No. 5,139,025 and in U.S. Pat. No. 5,217,013, which in some respects are more particularly directed to the use of such optical spectrophotometric procedures on the human head, in conjunction with examination of certain parameters and attributes of brain condition and function, in particular cerebral blood oxygen saturation. Accordingly, this last-mentioned copending application discloses and describes additional and other such "optical probes" or sensors which are particularly intended for (but not necessarily limited to) use on the human skull, for monitoring internal brain tissue and function through representative parameters.

The present invention is directed to improved and preferred forms of sensors for use in apparatus of the type just mentioned, as well as for potential use in other analogous such devices, providing further advanced and improved "optical probes" or patient interfaces, by which optical-response data is obtained from the patient and supplied to a spectrophotometric processing device. Prior participants in the art have addressed somewhat similar or analogous underlying considerations, and reference is particularly made to the work of Frans F. Jobsis et al, as represented in and by prior U.S. Pat. Nos. 4,223,680; 4,281,645; 4,321,930; 4,380,240; 4,510,938; and 4,805,623. While certain of the underlying concepts and/or scientific assumptions or theories set forth in these patents differ markedly from those addressed by the present invention, as reflected by the related and incorporated prior and copending patents and applications identified above, these prior patents attributed to Jobsis et al contain considerable information, etc. of interest to the general subject matter hereof, and certain such patents (in particular, U.S. Pat. Nos. 4,321,930, 4,380,240 and 4,510,938) expressly disclose patient sensor units in the form of headpieces for use in superficially similar in vivo optical spectrophotometric procedures. Accordingly, these and other such prior teachings provide background information of definite interest, and to some extent this may be said in connection with various sensors developed for use in arterial pulse oximeters and patented previously; for example, see U.S. Pat. Nos. 4,013,067, 4,865,038, 4,819, 752, 4,825,879, 4,928,691, 4,880,304, 4,964,408, and published PCT Application WO 89/09566.

BRIEF SUMMARY OF INVENTION

As indicated above, the present invention provides further improvements in optical spectrophotometric sensor assemblies, i.e., "optical probes", particularly adapted for in vivo use as the patient interface in clinical spectrophotometric patient-monitoring apparatus such as the aforementioned cerebral oximeter referred to in earlier U.S. Pat. No. 5,139, 025 and more particularly addressed in copending applications Ser. Nos. 711,147 and U.S. Pat. No. 5,217,013.

Accordingly, the major objectives of the invention, and the advantages attributable thereto, comprise the provision of new and improved forms of patient sensors for obtaining optical spectrophotometric data on an in vivo basis in clinical use, which include both general and particular features and attributes of such a device, comprising generally a flexible support or component-carrier adapted for comfortably conforming to the shape of the patient's cerebrum or other such anatomical area, with particular component-mounting structure and light-guiding and shielding apparatus for optimizing the introduction of selected light spectra into the patient and for enhancing the faithful and accurate detection of the low-level resulting light which produces the corresponding electrical signals processed to obtain the desired biomedical information.

Further, the invention provides certain improved forms of such a sensor, together with particular preferred componentry, including optical (light-emitting and detecting) components as well as mounting structure and light-guiding and shielding members and arrangements, within the environment of a generally soft, flexible outer envelope providing a support or carrier for the electro-optical components. In particular, a preferred form of light inlet and outlet means is provided for the light-emitting and light-detecting components of the sensor which defines non-distortable, shape-retaining light passages and provide novel light-shielding effects, to protect against distortion and attenuation of the optical response information which is obtained as a representation of, and which embodies, the desired physiologic data, but which must be converted into electrical signals and subjected to substantial processing in order to actually obtain the desired information.

The invention further provides novel structures and forms of the sensor body, and of the mounting (securement) means for the electro-optical components, and for the novel light-shielding means, to protect from optical distortion and interference during use in the anticipated environment and thereby further enhance the fidelity of the optical response data obtained, and in a broader sense to provide new and improved sensor structures per se, by which improved performance as well as improved and more economical manufacturing capabilities may be obtained. Further, the apparatus as disclosed is conducive to manufacture as either a disposable, single-use component or a reusable one which lends itself readily to customary and familiar clinical sterilization techniques, and thereby provides substantial economic advantage to both the medical service provider and the patient or insurer.

The foregoing major objectives, advantages and considerations of the invention, together with and including others, will become more apparent following consideration of the ensuing specification, particularly taken in conjunction with the appended drawings, briefly described hereinafter. Once again it is pointed out that the apparatus and methodology principally described hereinafter constitute merely preferred embodiments of the underlying invention, and do not specifically address other and further aspects thereof which will or may become further appreciated by those skilled in the art after consideration of the overall disclosure herein.

DESCRIPTION OF PREFERRED EMBODIMENTS

As stated above this application is related to U.S. Pat. No. 5,217,013 (among others), incorporated herein by reference, and it will be recognized that FIGS. 1–8 inclusive are directly similar to the corresponding figures of that application, modified nonetheless to show the improvements provided by the present invention. While the general underlying subject matter and basic nature of the apparatus of FIGS. 1–8 are thus fully described in this referenced and incorporated copending application, the following more limited description is provided for convenience.

Figures 1, 2:
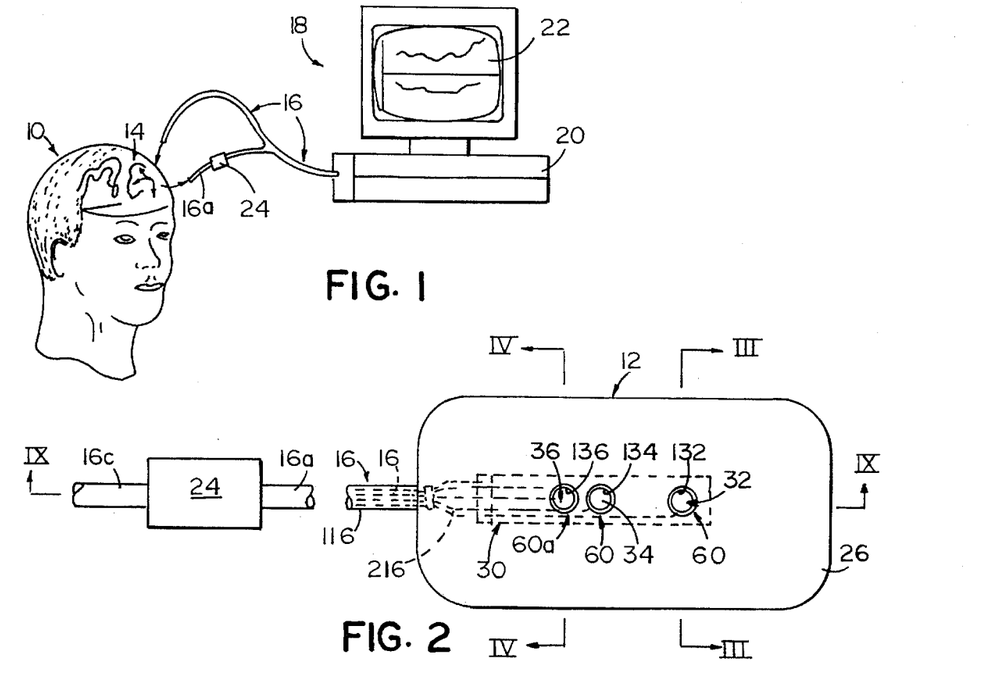
FIG. 1 is schematic pictorial representation showing a typical operative environment for apparatus in accordance with the invention, showing representative elements thereof.
FIG. 2 is a side elevation of one preferred embodiment of a sensor in accordance with the invention.
Figure 3:
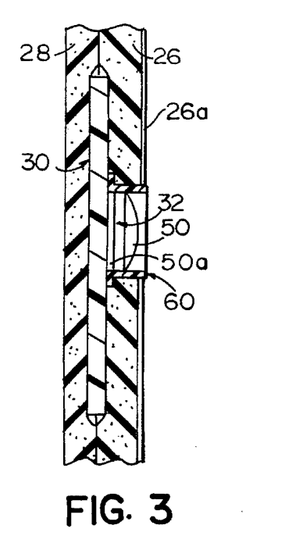
FIG. 3 is an enlarged transverse cross-sectional elevation taken along the plane III—III of FIG. 2.
Figure 4:
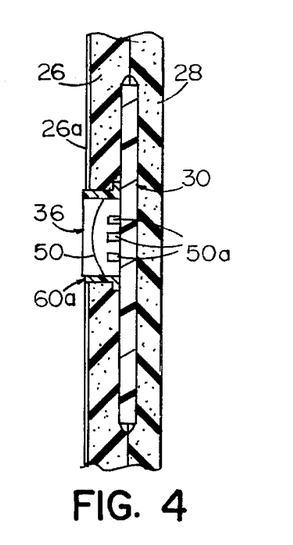
FIG. 4 is an enlarged transverse cross-sectional elevation taken along the plane IV—IV of FIG. 2.

FIG. 1 comprises a representative and pictorial showing of a typical clinical setting in which optical spectrophotometric apparatus in accordance with the invention is used, as part of an operative system for monitoring or examining patients. FIG. 1 is also shared with copending application Ser. No. 711,147, which describes a cerebral oximeter comprising an example of one such system, in considerable detail. For purposes of the present disclosure, it need only be said that FIG. 1 shows a human patient 10 who is being monitored by an optical spectroscopy processing unit 18 via a sensor unit 12 such as that shown in FIG. 2, which is applied to the forehead of the patient 10 to optically access an internal tissue volume or regional field 14 within the cerebrum, directly adjacent the point where sensor 12 is located, but inside of the scalp, skull, and adjacent dura, i.e., within the brain tissue itself. The sensor 12 is coupled to the spectroscopy unit 18 through a conductor bundle 16. As generally illustrated, the spectroscopy unit 18 includes a digital computer 20 having a monitor 22 on which visual displays may be perceived. It will be noted that the receiver (detector) conductor bundle portion 16a preferably includes an amplification unit 24 disposed a short distance away from the patient 10.

Generally speaking, the sensor 12 preferably comprises an elongated, somewhat rectangular member (FIG. 2) with rounded corners, from which the conductor bundle 16 extends outwardly. The particular embodiment of the sensor assembly shown in FIG. 2, designated by the numeral 12, comprises a laminar "sandwich" (FIGS. 3 and 4) which includes an outer layer (i.e., a cover) having a soft, flexible sheet of foam material or the like 26 on the side facing the patient, and a backing layer 28 which may be of the same material as that used for layer 26. The two layers 26, 28 are secured together adhesively, with an electrical component board 30, or at least the components themselves, without the board, disposed between them. Such components comprise electro-optical devices including photodetectors 32, 34 and a light source 36, which are disposed in registration with appropriate apertures 132, 134 and 136 extending through the foam layer 26 (FIGS. 3 and 4), through which such optical components may access the patient 10 (by emitting light which transmisses through the scalp, skull and brain tissue of region 14, and then detecting resultant light after it leaves such region and passes back out of the patient through the skull and scalp, etc.).

Figure 6:
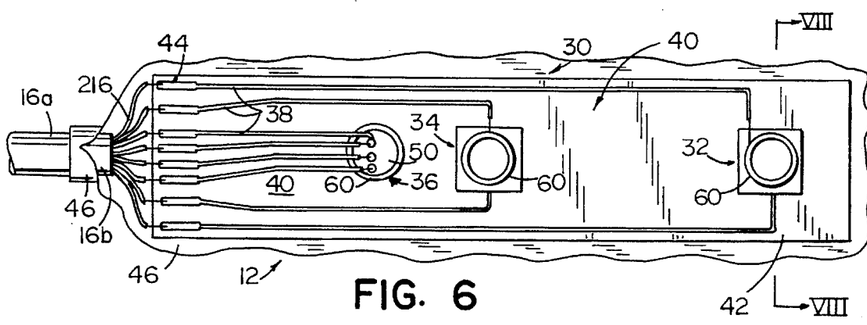
FIG. 6 is an enlarged side elevational view showing the circuit board and its electro-optical components, with certain of the electromagnetic shielding members in place and others partially removed.

The electrical component board 30 is preferably smaller in overall size than the outer dimensions of the foam layer 26 and backing layer 28, which provide the outwardly visible shape of sensor assembly 12 (as illustrated in FIG. 2). Component board 30 preferably includes a "printed circuit" board 40 such as that illustrated in FIG. 6; more particularly, a support substrate 40a, having printed conductor strips 38 secured to one side. Support substrate 40a also carries the aforementioned photodetectors 32 and 34, as well as the light source 36, all of which may be adhesively secured directly to the substrate and electrically connected to the respective conductor strips 38 by a small wire-like conductor 39 (i.e., wire bonded), in accordance with conventional procedures. In a preferred embodiment, the circuit board 40 may be of the readily flexible type known as a "flex circuit", and source 36 comprised of a closely-grouped series of light-emitting diodes (L.E.D.s) which are individually excited through particular individual conductor strips 38, i.e., strips 38a, 38b and 38c (FIG. 7), in conjunction with a common ground conductor 38d. The conductive strips of circuit board 40 are electrically connected to the adjacent portion 16a of conductor bundle 16 by soldering the end extremities of the electrical conductors (i.e., wires) 116 inside the conductor bundle 16a to the row of contacts 44 forming the end extremities of conductive strips 38, near one end of the board 40 (FIG. 6).

Figure 7:
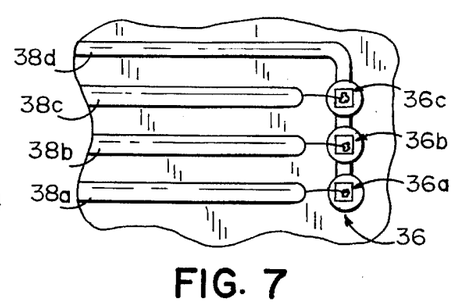
FIG. 7 is a fragmentary further enlarged view showing portions of the apparatus shown in FIG. 6.

As specifically shown in FIG. 7, there may be several different individual such L.E.D.s, designated 36a, 36b, 36c, each for producing a specifically selected different light wavelength. While it is also possible to implement the invention in other configurations, e.g., with remotely located light-producing elements and fiberoptic conductors and emitters, the preferred configuration illustrated provides certain advantages, particularly in conjunction with present-day L.E.D.s, which can provide surprising amounts of light intensity from a very small component with relatively low excitation.

As explained at some length in the above-noted copending and incorporated applications, the relative separation (distance between) the light source 36 and the two detectors 32, 34 is of considerable importance to the particular purpose, function and application of the optical spectrophotometric device with which the sensor assembly 12 is to be used, since these distances effectively determine the location and size of the particular internal region 14 which is to be selectably examined by the interrogating light wavelengths. However, in the broader aspects of the underlying invention, various such distances may be determined and specified without otherwise changing the overall nature of the apparatus and methodology.

In the particular embodiment and configuration referred to above and disclosed in detail in U.S. Pat. No. 5,217,013, the circuit board 40 is covered on both major sides with a thin, stiffly flexible conductive metal layer such as that shown at 42 in FIG. 5, which provides shielding against otherwise-disruptive or distorting influences such as electromagnetic or electrostatic fields as well as anomalous ambient light, etc. Layer 42 shown in FIG. 5 preferably comprises a thin sheet of copper which is of essentially the same outer dimensions as the circuit board 40 in the preferred embodiment, and is formed with apertures 232, 234 and 236 of a size and shape closely complementary to the outer periphery of the sensors 32 and 34, and the light source 36, respectively, i.e., the space immediately surrounding the L.E.D.s 36a, 36b, etc. The opposite side of circuit board 40 is also preferably covered by a shield layer 42' (FIG. 8) essentially similar to layer 42, although of course without the apertures since there are no electro-optical components on the reverse side of board 40. That is, the shielding layer 42' on the non, component side of circuit board 40 is simply an imperforate sheet of the same conductive material as layer 42, and both are preferably adhesively secured in place.

Figure 5:
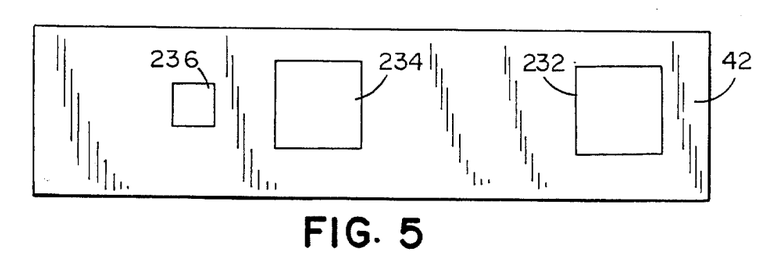
FIG. 5 is an enlarged side elevational view of a preferred form of shielding element for use in the apparatus.

The laminar "sandwich" described above which forms electrical component board 30 (including the circuit board 40 and its electro-optical components and oppositely-disposed shielding layers 42, 42') is preferably additionally shielded by use of an overlay of conductive sheet material such as a foil-like metal, e.g., copper tape, as designated by the numeral 46 (FIGS. 6 and 8), which is wrapped completely around the laminated "sandwich" on all sides except for closely-fitting apertures disposed in registration with apertures 232, 234 and 236 of mask layer 42 (FIG. 5). Conductor bundle 16a is preferably in the form of shielded "co-ax" cable, i.e., having a metallic mesh sleeve 16b (FIG. 2) which peripherally surrounds the electrical conductors 216 (which are mutually insulated from one another), and the sheath 16b (or an integral portion thereof) is extended toward and into contact with the outer shielding layer 42 of electrical component board 30, where it is soldered or otherwise secured in place. Sheath 16b is preferably disposed inside a generally tubular, rubber-like outer sleeve 116, which is preferably of an electrically insulating material and also serves aesthetic purposes.

Figure 8:
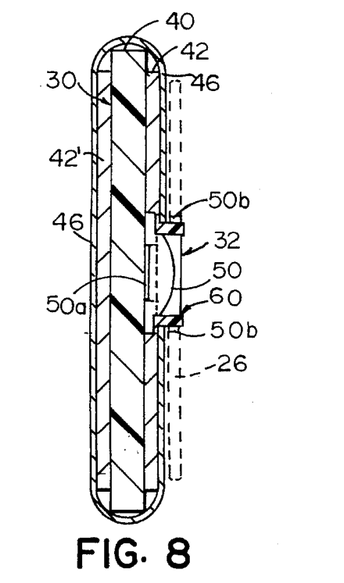
FIG. 8 is a further enlarged transverse cross-sectional elevation taken along the plane VIII—VIII of FIG. 6, showing the electromagnetic shielding in place.

Further general aspects of the sensor assembly 12 include the following. The frontal layer 26 should be of black, light-absorbing material, in order to more effectively isolate ambient light from the electro-optical components 32, 34, 36, as well as to help prevent any possibility of surface leakage between source 36 and detectors 32, 34. This helps ensure that photons received by the detectors have actually transmitted the tissue of the patient, and thus carry desired information. The rear layer 28 of the sensor assembly is also preferably opaque to ambient light, i.e., is of dense black material such as an imperforate sheet of polymeric material. In addition, at least layer 26, and preferably layer 28 as well, is of sufficiently open-celled character as to transmit water vapor from the patient, to prevent moisture build up between the outer face of layer 26 and the patient. One preferred type of such material is a polyurethane foam which is known commercially by the trademark "Poron", which is approved for medical applications (preferably, in the "Very Low Modulus" (i.e., very soft) grade, but of relatively high density (e.g., at least about twenty-five lb./cu. ft.)). Also, as noted in related U.S. Pat. No. 5,217,013, it is desirable to provide a small deposit of an optically clear material such as epoxy over the light source 36, i.e., the grouped array of L.E.D.s 36a, 36b, etc., as well as over the photodetectors 32, 34, thereby further augmenting the retention of these elements in place atop the circuit board 40. Primary attachment of these elements to board 40 is preferably accomplished by a thin layer of conductive (silver) epoxy 50a disposed beneath each such component, as shown in FIG. 8, and this is also advantageously used to interconnect the different shielding components (layers 42 and 42', as well as the foil layer 46) and secure them together into a unified shielding member, as well as to connect the latter to the shielding sheath 116 provided in cable 16.

As indicated above, in the actual usage of the sensor 12, it is applied to anatomical surfaces which are not likely to be perfectly flat, and which on the contrary are at least moderately curved; in fact, such curvature is likely to be compound in nature (i.e., not simply cylindrical), and the nature and extent of such curvature will vary from patient to patient, with a considerable degree of variation between some individuals. The present invention recognizes that, under such variations and amounts of curvature encountered in actual use, the particular instantaneous configuration of the apertures 132, 134 and 136 extending through the innermost foam layer 26, through which light must pass to communicate between the sensor 12 and patient 10, will change from one patient to another, as a function of the particular curvature which the sensor must embody in order to lie closely against and contiguous to the particular area of the particular patient involved. That is, although initially formed with a circular cross section, these apertures will be distorted in various different ways as the sensor is applied to the forehead (or other area) of each different patient and thus changed from planar to curved in shape. When applied to the forehead, the sensor is made to be generally concave, and the aperture will thus undergo widening in a direction transverse to the major axis of sensor curvature, with a corresponding narrowing along such axis. Of course, where complex, compound curvature is encountered (as is often or typically the case), the resulting changes in aperture shape are correspondingly complex.

The aforementioned changes in the actual shape of the light-passage apertures will thus change the amount of light which is actually supplied to and correspondingly received from each different patient, and this introduces a significant and fundamental non-uniformity between the optical response data obtained from one patient to another even though the electro-optical components themselves function exactly the same from patient to patient. Moreover, since the changes in light-passage aperture shape may cause either an effective narrowing or widening of the aperture involved, depending on the stress distribution around the aperture, the overall effect thus represents a basically unpredictable potential variation in the resultant light energy presented to the detectors, from which the latter produce corresponding electrical signals for further processing before the desired physiologic data can be obtained. Of course, any such variation is of a directly adverse nature which can only be expected to adversely affect system accuracy and efficacy, and is particularly undesirable in an in vivo spectrophotometric system such as that involved here, due to the extremely low level of resultant light energy available to the detectors in any event following the diffuse scattering and absorption effects attributable to the blood and tissue of the patient through which the light must pass prior to detection.

In accordance with the invention, means are provided by which the aforementioned adverse effects are overcome, and more particularly by which the passages through which light travels to and from the patient are maintained in a uniform size and shape regardless of the manner in which the remainder of the sensor 12 is contorted in actual use. While potentially implemented in varying ways, a preferred form of such means is illustrated in the various figures of the drawings, and may be seen to comprise a generally cylindrical, tubular member 60 which functions as a non-distortable light passage disposed coaxially inside the apertures 132, 134 and 136 which extend through the outer layer 26, and preferably mounted so as to preclude leakage of light at any point between patient and the associated electro-optical component, as explained hereinafter.

Figure 9:
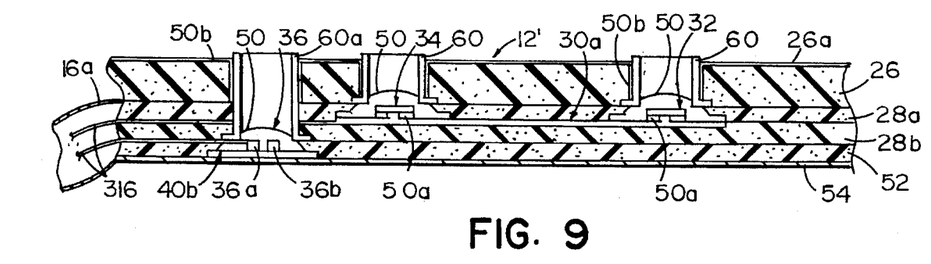
FIG. 9 is an enlarged longitudinal cross-sectional elevation taken along the plane IX—IX of FIG. 2, showing another embodiment of the invention.
Figure 10:
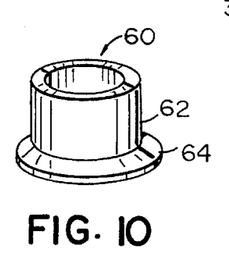
FIG. 10 is an enlarged perspective view of a single light-passage and shield member, shown apart from the other structure with which it is used in accordance with the invention.
Figure 11:
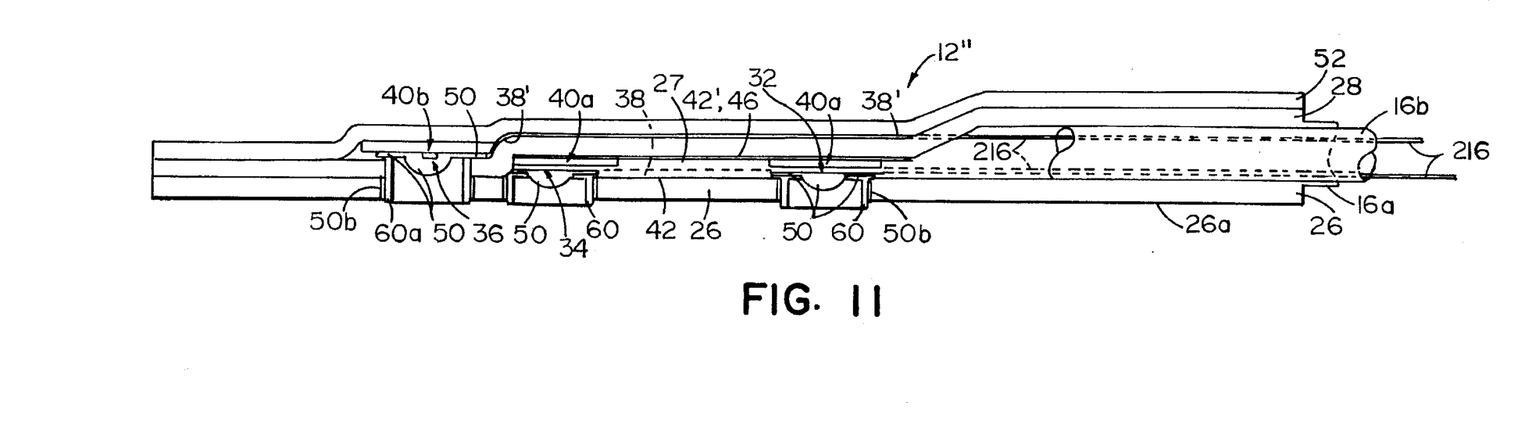
FIG. 11 is an enlarged longitudinal cross-sectional elevation similar to that of FIG. 9 but showing a further embodiment of the invention currently considered to represent a preferred embodiment and best mode thereof.
Figure 12:
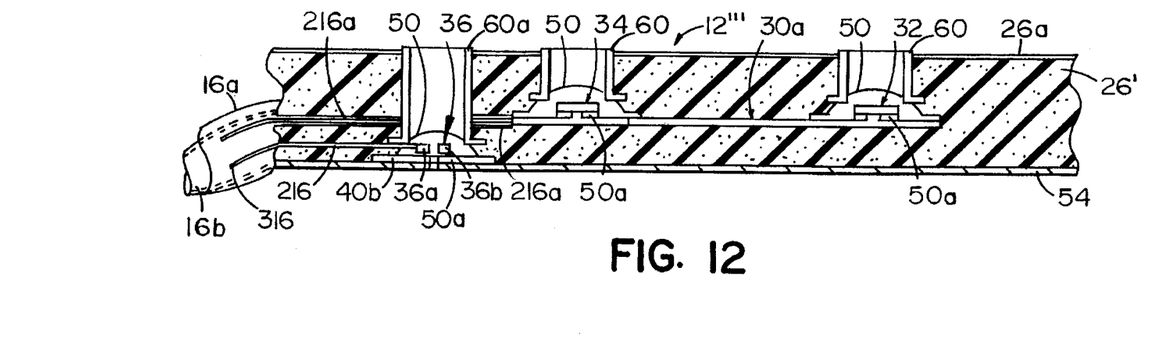
FIG. 12 is a further enlarged cross-sectional elevation similar to FIG. 9 but showing a still further embodiment of the invention employing a substantially one-piece unitary body representing another preferred embodiment and potential best mode of employing the invention.

The preferred configuration of the light-passage components 60, 60a is generally illustrated in FIG. 10, from which it will be seen that these elements preferably include a barrel-like tubular shank 62 with an integral flat, annular end flange 64. While various specific materials may be used for this element, they should be substantially rigid and non-deformable, at least under the type and extent of stresses typically encountered in the usage and application here involved, and they should be opaque to the light energy wavelengths involved and, preferably, have white or other optically reflective surfaces inside the light passage portion. Also, it is desirable that they be lightweight and inexpensive. One particular satisfactory material is the well-known industrial plastic "Delrin", but other satisfactory materials are no doubt also available. The basic preferred positioning for the light passage components 60 relative to the other members which make up the sensor assembly 12 can readily be seen in the various drawings, but it will be noted that FIGS. 9, 11 and 12 depict a somewhat different embodiment than FIGS. 3, 4, 6 and 8, and the particulars relative to each such embodiment are set forth below.

As disclosed in referenced and incorporated U.S. Pat. No. 5,217,013, the electro-optical components (photodetectors 32, 34 and L.E.D. grouping 36) may be mounted directly atop the electrical board 40 (FIGS. 3, 4, 6, 7 and 8), preferably by use of optical-grade epoxy 50 which may be applied to form a dome-like covering over the entire component or component grouping involved. In such an embodiment of the invention, the light-passage elements 60 may be secured in the same manner, and at the same time, using the epoxy deposit 50 to secure both the element 60 and the associated electro-optical component to one another and to the underlying circuit board. As illustrated in these figures, the inside diameter of the elements 60 preferably generally corresponds to the outside diameter of the electrooptical component or component grouping involved, and the end flange 64 of each such element is preferably in close contact with the surface of the circuit board. As shown in FIGS. 8, 9, 11 and 12, the epoxy deposit 50 preferably includes a thin layer which underlies the end flange 64 of the associated light-passage elements 60, 60a. Further, the epoxy 50 may include a thin annular portion 50b which secures the edges of the apertures 132, 134 and 136 in the outer foam layer 26 to the closely adjacent outer end extremity of the barrel 62 of each element 60.

FIG. 9 depicts, in somewhat simplified form, certain variations in the overall structural arrangements referred to above, which embody and illustrate an alternative embodiment that among other things, provides increased optical isolation between the source 36 and the photodetectors 32, 34. As will be immediately apparent, the sensor assembly 12' of FIG. 9 shows the photodetectors 32, 34 at a first level relative to the overall depth or thickness of the assembly, analogous to the arrangement of the other figures, and the light source 36 disposed at a different level, substantially below the detectors and in fact outside both layers 26 and 28. In this configuration, the light passage element 60a associated with the source 36 is considerably longer than the elements 60 associated with the photodetectors 32, 34, which must only extend through the single layer or thickness 26. Also, the detectors 32, 34 in this configuration may be mounted atop a circuit board 30a which is not as long as the analogous board 30 used in the previous embodiment, and which terminates essentially at the perimeter of detector 34. Thus, circuit board 30a does not extend to the area of source 36, and the latter is not mounted upon such circuit board at all. On the contrary, source 36 is preferably secured in place relative to the other components of sensor 12' merely by the epoxy deposit 50, which covers the individual L.E.D. elements 36a, 36b, etc., and also embeds the innermost extremity of the light-passage element 60a, i.e., its end flange 64. Of course, the source L.E.D.s 36a, 36b, etc. require electrical excitation, and thus may be coupled into cable 16 by individual conductors 316, which are essentially analogous to the conductors 216 referred to in conjunction with FIGS. 2 and 6. While it would of course be possible to implement conductors 316 by using a second circuit board or flex circuit, this is not currently regarded as being particularly necessary, and it would represent increased cost.

It will be observed that sensor assembly 12' shows the second or backing layer 28 divided into two component parts, 28a and 28b, which may be done to facilitate mounting of the detectors 32 and 34 on circuit board 30a, together with their corresponding light-passage elements 60. That is, in assembling this embodiment of the sensor assembly the detector light-passage elements 60 may be inserted into the corresponding apertures provided in outer layer 26, while the detectors themselves are secured in place upon circuit board 30a by their respective epoxy deposits 50, together with thin layers of conductive epoxy 50a extending beneath each detector and directly adhering them to their respective conductors on circuit board 30a. Upon deposit of the epoxy portions 50, layers 26 and 28a are secured together by a thin layer of contact adhesive disposed therebetween), with the end flange portions 64 of each light-passage element 60 embedded in the corresponding epoxy deposit 50, whereby the light passage elements are immovably secured to their respective detector elements. The second portion 28b of the outer layer 28 may then be adhered in place against layer 28a and board 30a, and the second light-passage element 60a inserted through its corresponding aperture in the resulting three layer assembly. Following this, the L.E.D. elements comprising source 36 are secured in place to a further layer 52 (which is also a flexible, opaque polymeric material), and layer 52 then adhered in place against layer 28b, as by another layer of pressure-sensitive adhesive disposed therebetween, with the end flange 64 of light passage element 60a embedded in the corresponding epoxy deposit 50 to immovably secure element 60a to the source 36. As a final measure, an outer cover layer 54 may be similarly adhered in place by use of pressure-sensitive contact adhesive, and this outer f layer should also be an opaque polymeric or the like having flexibility comparable to that of the other layers.

As pointed out above, the alternative embodiments depicted in sensor assembly 12' provide for a greater degree of optical isolation between the source 36 and detectors 32, 34, which can be a very important attribute. In this regard, it should be noted that the absence of a continuous circuit board extending beneath and common to all of the electro-optical components tends to significantly reduce optical leakage and "cross-talk" therebetween, as does the increased amount of essentially continuous opaque material between the source and detectors made possible in this way and further increased by positioning these components at difficult levels within the sensor body. At the same time, however, the principal features of arrangement and construction embodied in sensor assembly 12' should not necessarily be regarded as usable only in this particular arrangement, and the same is generally true with respect to the corresponding features and attributes of sensor assembly 12, discussed in conjunction with the prior figures. That is, the variations in circuit board arrangement and disposition may in fact be implemented in either such version as well as others which are also possible, and the same is true with respect to the different mounting positions of the electro-optical components, with their corresponding different optical passage elements 60 and 60a. It should be noted in this regard that, while not specifically shown in FIG. 9, the alternative sensor arrangement 12' should also include the shielding layers 42, 42' and 46 referred to above and shown in the embodiment of FIGS. 3–8, which may be analogously implemented inside the polymeric or other such layers shown and electrically connected into sheathing such as that shown at 16b in FIG. 2 (not specifically shown in FIG. 9) which comprises part of the cable 16.

It is to be further and expressly noted that the variations represented by both sensor assemblies 12 and 12' may if desired exclude all use of a circuit board of the type designated 30 or of the type designated 30a, since conventional conductors may be used to make the necessary electrical connections, and the detectors 32, 34 (which may or may not be provided on small individual circuit boards or like supports) secured in place directly to the flexible layers or members 28a and 28b, as by epoxy 50 or other adhesive, in the same general manner as the source 36. An example of such a structure is shown in FIG. 11, described more fully hereinafter. Furthermore, the sensor body (i.e., the soft flexible polymeric or other such portions) may, in a potentially most-preferred form, be provided in a more monolithic form, and even as a one-piece integrally molded part, rather than in the illustrated layered constructions. An example of such an integral, one-piece part is shown in FIG. 12, also referred to in more detail hereinafter. Such a one-piece structure will potentially simplify manufacture considerably, and probably also achieve other economies as well; furthermore, it will or may make resterilization and reuse possible, and thus help reduce hospital operating costs. This goal will be more readily achieved if the electro-optical components are sealed in place and not exposed to the environment, and this may be accomplished by embedding them integrally (with their connective wiring, shielding, etc.) inside either an integrally molded or a permanently joined and completely sealed laminate body structure, in which light-passage elements like those designated 60, 60a are either permanently molded in place or else secured to their surrounding structure and respective components, in the same general manner as discussed above, in which deposits 50 of epoxy or the like act to seal the component from local contamination. While it would also be potentially advantageous to have replaceable components in a reusable sensor, this could be accomplished by (for example) providing molded-in or other such hermetically sealable interior compartments for each electro-optical component, to which access would be available when and if necessary but which otherwise would remain sealed and hence uncontaminated. While the relative placement and distance between each of the two sensors 32, 34, and between the sensors and the source 36, is important in the most preferred spectroscopic system 18 (as extensively explained in referenced copending application Ser. No. 711,147 and issued U.S. Pat. No. 5,139,025), these distances may in fact be established and maintained with acceptable accuracy and consistency by the positioning and use of the light-passage elements 60, 60a, with their corresponding apertures extending through layers 26 and 28 and/or through the analogous portions of an integrally molded or similar generally monolithic sensor body.

As indicated above, FIG. 11 illustrates a further embodiment 12" of the sensor in accordance with the invention, which represents a structure presently contemplated to be the preferred embodiment and best practical mode of implementing the invention. As may be perceived upon consideration, the embodiment 12" is somewhat similar to the embodiments 12 and 12' discussed above in conjunction with FIGS. 2–8 and 9, and particularly to that of FIG. 9, in that it utilizes individual layers 26, 28 and 52, which are adhesively secured in back-to-back laminate form, with the electro-optical source 36 and receivers 32, 34 mounted between the various layers; more particularly, with source 36 disposed between different layers and located more deeply within the laminate body than the receivers 32, 34. While many of the elements and components utilized in embodiment 12" are directly comparable to those of the preceding figures, and therefore carry analogous numbering of analogous components, it will be noted that certain differences do nonetheless exist from the embodiments 12 and 12' shown and described previously.

In particular, the sensor embodiment 12" utilizes three layers (26, 28 and 52) of generally soft, flexible material (which may like that discussed in the preceding embodiments comprise the commercially available cellular urethane known as "Poron"), and the different layers are each generally continuous, but curved directly around the electro-optical components to integrally embody them in the resulting unitary structure. Further, it will be noted that in the illustrated version of this embodiment receivers 32, 34 are carried on separate circuit boards 40a, which are not a continuous member such as that shown in the embodiment 12' of FIG. 9. Further, source 36 is also carried on its own separate circuit board 40b. Once again, the electro-optical components themselves may be secured atop their respective boards by a layer of conductive epoxy or the like and wire-bonded or otherwise connected to their respective conductors 38, 38', but these conductors will constitute individual wires that extend outwardly (to the right, as shown in FIG. 11) away from the corresponding components, and lie between adjacent layers of the flexible material constituting the body, ultimately emerging between layers 26 and 28 as conductors 216, at which point the latter extend inside the sheathed conductor cable 16a, which is directly and adhesively secured in place between layers 26 and 28.

Like embodiment 12' of FIG. 9, the embodiment 12" of FIG. 11 preferably incorporates non-deformable light-passage members 60, 60a, which are also preferably retained in place by epoxy deposit 50 which, in addition to forming a dome over the corresponding electro-optical component itself, also extend beneath the outer flange 64 of each such passage component, tightly securing it to the upper side of the individual circuit boards 40a, 40b. Once again, at least the outer layer 26 is preferably secured around the outer periphery of the light-passage elements 60, 60a by a layer of epoxy or other suitable adhesive, designated 50b. Unlike the preceding embodiments, the use of separate and independent circuit boards 40a for the detectors 32, 34 of embodiment 12" would provide a space therebetween, and that is preferably filled with a particularly-shaped portion 27 of the same flexible material as layers 26 and 28, which is disposed directly between these two layers as a spacer and optical isolation member. Furthermore, the embodiment 12" incorporates internal shielding members 42, 42' and 46 directly analogous to those shown in FIGS. 3, 4 and 8, but which extend closely around only the detectors 32, 34 and their corresponding individual circuit boards 40a, folded closely around the left end of the board 40a carrying detector 34, and disposed closely and snugly against the knee-shaped bend formed in layer 28 at this point, on whose opposite side is disposed the board 40b for source 36. As may be seen in FIG. 11, the shielding layers 42, 42' and 46 extend to the right, on opposite sides of the spacer portion 27 and generally following the oppositely-disposed inner surfaces of layers 26 and 28 to the outer periphery of the sheathing 16b which extends coaxially about conductors 216, at which point the shielding layers 42, 42' and 46 are all secured to one another and to sheathing 16b, for example by use of conductive epoxy.

As may be appreciated, embodiment 12" thus provides a somewhat simpler and potentially thinner, more lightweight and more flexible sensor structure, which is also potentially more easily and economically manufacturable. In this regard, the thickness of the layers 26, 28 may be about 0.045 inch, and that of layer 52 about 0.035 inch; accordingly, the total thickness of sensor 12" (like that of the other illustrated embodiments) at the end opposite cable 16 is merely about one-eighth inch, and even the center thickness is not much more than this since the electro-optical elements and their circuit boards are very thin, particularly where "flex circuits" are used. Similarly, all embodiments of the sensor are extremely lightweight when constructed in accordance herewith, sensor 12" for example being not more than one-half oz. in total weight, including all operating components and shielding layers (but without the electrical cable 16) even where it is made somewhat oversized, i.e., approximately three and one-half inches long by one and three-quarter inches wide. As in the preceding embodiments, embodiment 12" preferably carries an integral layer of pressure-sensitive adhesive 26a on the outer surface of layer 26, by which it may be attached to the forehead or other desired area of the patient.

A further embodiment 12''' of the invention is illustrated in FIG. 12, which may provide even further advantages and economies in manufacture, as well as in use, although nonetheless having relatively analogous elements and features to those of the embodiments already discussed, particularly the embodiment 12' of FIG. 9. With further reference to embodiment 12''' of FIG. 12, which also carries similar numbering for similar or analogous components, it will be seen that this embodiment constitutes a unitary, one-piece integrally molded (or extruded) body of lightweight, flexible foam or the like, for example cellular urethane foam directly similar to that utilized in the "Poron" material referred to above. Due to the one-piece nature of the resulting article, an outer cover or label 54 is shown adhered in place, but it should be understood that this is not at all essential and is only shown as an example of a further aspect which may be included in such a device, for primarily esthetic or other such reasons.

While the componentry and overall structural arrangement of the sensor embodiment 12''' is analogous to the multi-layered embodiments referred to above, the manufacture and assembly of the sensor is significantly different since the electro-optical components are preferably integrally enclosed within the one-piece flexible body of the sensor by molding the body directly around the components. Thus, the soft, flexible one-piece body portion of sensor 12''' may be a monolithic structure, or it may be comprised of two or more particular types or kinds of foam or other such flexible polymer, joined integrally together by coextrusion or comolding procedures, where different durometers or even different materials are to be used to provide different characteristics in different parts of the resulting one-piece structure. In any such case, the electro-optical components are integrally mounted in place. Such a structure has the signal advantage of being reusable, since all of the components are in effect sealed from ambient contamination and the entire structure lends itself to known sterilization techniques currently employed in hospitals and other such health facilities.

While the basic nature and attributes of the embodiment 12''' will be understood from the comments just made, together with the preceding discussion of other embodiments, it should be pointed out that this embodiment may potentially use any of the three arrangements of circuit boards discussed above in conjunction with the other embodiments, and may incorporate either of the relative source-detector locations shown in the preceding embodiments, depending upon whichever is viewed as most advantageous from the standpoint of overall manufacture and operation. Of course, it will be understood that where the electro-optical components are molded directly in place inside the one-piece body, the epoxy deposits 50, as well as the light-passage elements 60, 60a, will be assembled with their corresponding component before the body is molded around the resulting component assembly. Alternatively, the one-piece body may be molded separately, with integral conductors disposed in proper position and corresponding well-like apertures provided as voids in the molded structure, whereby the electro-optical component assemblies may subsequently be inserted in place and secured, if necessary, by conductive adhesive to the internal conductors, as well as by non-conductive, opaque epoxy or other adhesive disposed around the outer periphery of the barrel portion of each light-passage element 60, 60a, establishing a light-tight seal between it and the adjacent molded structure as well as securing the two together.

As may be understood and appreciated from the foregoing disclosure, the light-passage elements 60, 60a will in each embodiment function to ensure direct and repeatable consistency in the actual size and shape of the light passage established between the electro-optical components and the patient 10 regardless of the various configurations into which the sensor may be shaped in conforming it to a particular surface area of a particular patient 10. This consistency applies to the effective distance between the skin of the patient and the location of the sensor and receiver, as well as to the cross-sectional size and shape of the light passage.

At the same time, leakage of light from around the sides or the end of the passages so established is substantially precluded, regardless of whether the source for such light happens to be the internal source 36 of the sensor or external, ambient sources which might otherwise provide errant light that could reach the detectors in one manner or another and introduce error. That is, when the sensor is applied to the skin of the patient, and resiliently shaped into conformity with the particular shape of the area involved, the adhesive layer 26a on the outside of layer 26 will adhere the entire sensor snugly in place, with the outer end extremity of each of the light-passage elements 60, 60a essentially flush against the skin of the patient but in fact preferably protruding at least slightly into the surface of the skin for enhanced optical coupling and relative isolation. Since the outer layer of adhesive 26a extends directly up to the outer periphery of the light-passage elements 60, 60a, and the outer layer 26 is preferably adhesively secured to the latter as well, there is no opening outside the light passages through which light may pass between the patient and the sensor or detectors, and the only available passage is that defined by the elements 60, 68a, which as just stated are adhesively secured in direct contact with the skin of the patient.

In addition, even in instances where the operator of system 18 applies pressure to the rear surface of the sensor (i.e., to the outside of layer 28 or the outer cover 54), in order to hold the sensor tightly against the forehead or other selected area of the patient, the effective distance between the sensor or detector and the skin of the patient cannot be changed, as would of course be the case where the electro-optical components are simply mounted within resilient foam or other such layers that will readily yield when subjected to compressive forces. This is also true even where the electro-optical components are not mounted on the same circuit board or on any circuit board at all, as pointed out in connection with FIG. 9, since the length of the light passage elements 60, 60a will remain consistent in each case. Accordingly, system accuracy is very substantially enhanced, since non-uniformity attributable to these reasons is substantially eliminated. In furtherance of these desired ends, it may be noted that the outermost end extremities of the light-passage elements 60, 60a, preferably lie flush with, or extend slightly beyond, the outermost boundary of layer 26, i.e., these elements preferably extend through both the foam layer 26 and the thin layer of pressure-sensitive adhesive 26a disposed thereon, and very slightly beyond.

It is to be pointed out once again that while the foregoing disclosure addresses a particular preferred embodiment, and best mode, the apparatus in accordance with the invention, and that the various recited detailed aspects thereof are regarded as being important to the most preferred version of the particular sensor described herein to illustrate the principles and concepts involved in the invention, other embodiments and versions of the invention may well be appropriate in other circumstances. It is therefore to be understood that the foregoing description of a particular preferred embodiment is provided for purposes of description and illustration, and not as a measure of the invention, whose scope is to be defined solely by reference to the ensuing claims. Embodiments of the invention differing from those set forth above which nonetheless utilize the underlying concepts of the invention and incorporate its spirit should therefore be considered as within the scope of the claims appended below, unless such claims by their language specifically state otherwise.

The embodiments of the invention in which an exclusive property or privilege is claimed are defined as follows:

1. An optical sensor unit for use as a patient interface in obtaining spectrophotometric data during in vivo examination, comprising in combination:

a body having at least one side comprising a soft and deformable material providing at least limited longitudinal and lateral flexibility for conforming to the surface topography of a selected area on a patient;

an electrically actuated light source carried on said body, for producing and emitting light of selected wavelengths to irradiate internal patient tissue after passing through said surface;

at least one electrically responsive light-detector carried on said body at a particular spacing from said light source, for receiving resultant light of said selected wavelengths from said patient after passage thereof through said internal tissue and producing corresponding electrical signals; and a generally tubular and substantially non-deforming light-transfer member disposed in direct alignment with at least one of said source and detector and having a first open end portion disposed immediately adjacent thereto and in generally concentric alignment therewith, said light-transfer member extending from the location of said at least one source and detector through at least portions of said deformable material and having a second open end disposed to contact said patient and convey said light thereto, said, non-deforming light-transfer member having an open internal passage extending between said first and second open ends and being non-deforming to retain its initial size and shape throughout use during patient examination and provide a light-transfer passage of constant and unchanging size and shape throughout the distance between said patient and said at least one source and detector and through said at least portions of said deformable material regardless of the deformation imparted to said deformable material in operably conforming the sensor to a particular patient surface topography, said tubular light-transfer member having an overall axial length at least as great as the thickness of a wall of said light-transfer member measured in a radial direction.

2. An optical sensor as recited in claim 1, wherein said light-transfer member has generally opaque walls defining said open passage.

3. An optical sensor as recited in claim 2, wherein said walls defining said passage have optically reflective surfaces along said passage.

4. An optical sensor as recited in claim 1, wherein said member includes a generally regular and continuous tubular portion defining said open passage.

5. An optical sensor as recited in claim 4, wherein said generally tubular portion is disposed in an aperture extending through said one side and is secured in place with respect thereto.

6. An optical sensor as recited in claim 5, including means for sealing said tubular portion in substantially light-tight relation with respect to said aperture.

7. An optical sensor as recited in claim 5, wherein said portion extends at least slightly beyond the outer surface of said deformable material.

8. An optical sensor as recited in claim 1, wherein said body comprises a layered structure having at least two layers secured to one another.

9. An optical sensor as recited in claim 1, wherein said body includes a primary strata comprising a one-piece molded structure of flexible material, said molded structure carrying said light source and said light-detector and defining a pair of open passages, each of said passages extending from a different one of said source and detector through said primary strata.

10. An optical sensor as recited in claim 1, including means defining at least a pair of said passages each providing a separate passage for a respective one of said source and said detector.

11. An optical sensor as recited in claim 10, wherein said means comprises a pair of generally rigid tubular members defining said passages and said passages comprise openings.

12. An optical sensor as recited in claim 11, wherein said tubular members are open-ended, and including means for connectively sealing one open end of each of said tubular members in substantially light-fight relation with its respective source or detector.

13. An optical sensor as recited in claim 12, wherein said tubular members extend substantially through said deformable material, and including means for sealing said members in substantially light-tight relation with respect to said material.

14. An optical sensor as recited in claim 12, including means for securing said tubular members to at least portions of their respective source and detector.

15. An optical sensor as recited in claim 1, including at least one thin sheet-like member of electrically conductive material extending around at least portions of said detector to shield it from ambient sources of electric and magnetic noise and distortion, said shield member disposed on the opposite side of said deformable material from that which contacts said patient.

16. An optical sensor as recited in claim 15, wherein said light-transfer member extends through said thin shield member.

17. An optical sensor as recited in claim 1, further including a circuit board underlying and carrying at least said detector, said board supporting said light-transfer member.

18. An optical sensor as recited in claim 17, wherein said light-transfer member is secured to said circuit board.

19. An optical sensor as recited in claim 18, wherein said light-transfer member is connected in light-tight relation to said deformable material.

20. An optical sensor as recited in claim 17, including at least one thin sheetlike member of conductive material extending around at least portions of said detector and of said circuit board to shield such portions from ambient sources of electric and magnetic noise and distortion, said shield member disposed on the opposite side of said deformable material from that which contacts said patient.

21. An optical sensor as recited in claim 20, wherein said light-transfer member extends through said thin shield member.

22. An optical sensor as recited in claim 21, wherein said light-transfer member is secured to said circuit board.

23. A thin, lightweight, highly compliant and conformable electrically-operated optical sensor having constant and non-distorting light-transmittal passages, for use with clinical spectrophotometric patient-examination apparatus, comprising:

a primary strata comprised of soft and readily deformable material, said strata having a first side for conformably contacting a selected surface area on said patient, a second side opposite the first, and a plurality of passages extending between said sides for transmitting selected light wavelengths to and from said patient through said primary strata;

at least one thin, lightweight and flexible substrate member disposed adjacent to and at least partially covering said second side of said primary strata, said primary strata and said at least one substrate member secured together to form a flexible and readily conformable patch-like sensor body for application to said selected area;

at least two electrically operated light-responsive optical components disposed generally between said primary strata and said at least one substrate member and secured in alignment with respective individual such passages, including a first such component to produce and transmit said selected light wavelengths in response to electrical signal actuation and a second such component to receive said wavelengths and produce corresponding electrical signals; and means defining a non-compliant and substantially non-distortable light-transfer element disposed in at least one of said passages, for conveying said selected wavelengths therethrough to or from said optical components along a light-transfer path having fixed and unchanging geometry despite deformation of said sensor body in conforming it to said selected area, said light-transfer element having a wall surrounding and defining said light-transfer path, said wall having a thickness at one end measured in a direction perpendicular to said light-transfer path that is less than the overall length of said light-transfer element.

24. A thin, lightweight, compliant optical sensor as defined in claim 23, wherein said optical components are secured to at least one of said primary strata and said substrate member.

25. A thin, lightweight, compliant optical sensor as defined in claim 23, wherein said at least two optical components are mounted generally independently of one another and separately secured in alignment with corresponding separate ones of said light-transfer elements.

26. A thin, lightweight, compliant optical sensor of claim 25, wherein said transfer elements comprise open-end tubular members and said at least two optical components are secured directly to an open end of their said corresponding separate light-transfer elements.

27. The thin, lightweight, compliant optical sensor of claim 26, wherein at least one of said at least two optical components is at least partially secured in position by direct attachment to at least one of said primary strata and said substrate member.

28. The thin, lightweight, compliant optical sensor of claim 26, wherein at least one of said at least two optical components is at least partially secured in position by said direct securement to its corresponding light-transfer element.

29. The thin, lightweight, compliant optical sensor of claim 25, wherein at least one of said electro-optical components is disposed further from said first side of said primary strata than another of said components and the light-transfer element associated with said further component is longer than the light-transfer element associated with said other such component.

30. The thin, lightweight, compliant optical sensor of claim 23, wherein said light-transfer element defines an open-ended passage at the location where it contacts said patient.

31. The thin, lightweight, compliant optical sensor of claim 30, wherein said light-transfer element comprises a hollow tubular member.

32. A thin, lightweight, compliant optical sensor of substantially unitary construction, for use with clinical spectrophotometric patient-examination apparatus, comprising:

a primary strata formed as a thin, generally flat one-piece member of soft deformable material, said strata having a first side for conformably contacting a selected area on said patient, a second side opposite the first, a plurality of integral mounting stations for electrically operated light-responsive optical components for transmitting and receiving selected light wavelengths, and light-transmissive passages extending through at least portions of said primary strata and said first side thereof for communicating said light wavelengths to and from said patient;

at least two of said electrically operated optical components, each disposed at a corresponding mounting station on said primary strata to transmit or receive said selected light wavelengths; and means for securing said optical components in place on said mounting stations and for sealing said components from ambient contamination;

said primary strata comprising an integrally molded member having said mounting stations molded in place therein, and said light-transmissive passages including passage defining means defining a substantially non-compliant and non-distortable light-transfer passage in said primary strata for conveying said selected wavelengths therethrough along a path having fixed and unchanging geometry despite deformation of said sensor in conforming it to said selected area, said light-transfer passages having an opening extending through at least portions of said molded member, said passage deriving means having a wall surrounding and defining said light-transfer passage, said passage defining means having a length that is at least as great as a thickness of said wall measured at one end.

33. A thin, lightweight, compliant sensor as defined in claim 32, wherein said at least two optical components are mounted generally independently of one another and separately secured to separate ones of said mounting stations.

34. A thin, lightweight, compliant optical sensor as defined in claim 32, wherein said optical components are molded into said primary strata.

35. A thin, lightweight, compliant optical sensor as defined in claim 32, including a generally rigid tubular member disposed in said one-piece member and defining said opening.

* * * * *

UNITED STATES PATENT AND TRADEMARK OFFICE
CERTIFICATE OF CORRECTION

PATENT NO. : 5,584,296
DATED : December 17, 1996
INVENTOR(S) : Cui, et al

It is certified that error appears in the above-identified patent and that said Letters Patent is hereby corrected as shown below:

Column 1, line 6;
    "December 10, 1992" should be --December 01, 1992--.

Column 9, line 42;
    Delete "f".

Column 15, line 54;
    "light-fight" should be --light-tight--.

Column 16, line 16;
    Before "conductive" insert --electrically--.

Column 17, line 11;
    "open-end" should be --open-ended--.

Column 17, line 26;
    Delete "electro-".

UNITED STATES PATENT AND TRADEMARK OFFICE
CERTIFICATE OF CORRECTION

PATENT NO. : 5,584,296
DATED     : December 17, 1996
INVENTOR(S) : Cui, et al

It is certified that error appears in the above-identified patent and that said Letters Patent is hereby corrected as shown below:

Column 17, line 42;
    "fiat" should be --flat--.

Column 18, line 28;
    "deriving" should be --defining.

Column 18, line 32;
    After "compliant" insert --optical--.

Signed and Sealed this

Sixth Day of January, 1998

Attest:

BRUCE LEHMAN

Attesting Officer    Commissioner of Patents and Trademarks